(12) United States Patent
Simard

(10) Patent No.: US 8,546,331 B2
(45) Date of Patent: *Oct. 1, 2013

(54) MODULATION OF PATHOGENIC CD14+/CD16+ MONOCYTES

(75) Inventor: John Simard, Austin, TX (US)

(73) Assignee: XBiotech, Inc., Vancouver (CA)

( * ) Notice: Subject to any disclaimer, the term of this patent is extended or adjusted under 35 U.S.C. 154(b) by 0 days.

This patent is subject to a terminal disclaimer.

(21) Appl. No.: 13/545,166

(22) Filed: Jul. 10, 2012

(65) Prior Publication Data

US 2012/0276110 A1 Nov. 1, 2012

Related U.S. Application Data

(63) Continuation of application No. 12/559,019, filed on Sep. 14, 2009, now Pat. No. 8,242,074.

(60) Provisional application No. 61/096,563, filed on Sep. 12, 2008.

(51) Int. Cl.
| | |
|---|---|
| A61K 39/395 | (2006.01) |
| G01N 33/15 | (2006.01) |
| C12N 5/0786 | (2010.01) |
| C07K 16/24 | (2006.01) |
| C12P 21/08 | (2006.01) |

(52) U.S. Cl.
USPC ............... 514/12.2; 424/130.1; 424/145.1; 435/7.24; 435/343; 530/388.23; 530/388.7

(58) Field of Classification Search
None
See application file for complete search history.

(56) References Cited

U.S. PATENT DOCUMENTS

| | | | |
|---|---|---|---|
| 6,623,736 B2 | 9/2003 | Tobinick | |
| 7,105,183 B2 * | 9/2006 | McGrath | 424/661 |
| 7,718,674 B2 | 5/2010 | Aberg | |
| 2003/0175832 A1 * | 9/2003 | Marton et al. | 435/7.21 |
| 2005/0276807 A1 | 12/2005 | Skurkovich | |
| 2006/0127407 A1 | 6/2006 | Chen | |
| 2009/0258070 A1 | 10/2009 | Burnier | |
| 2009/0291081 A1 | 11/2009 | Hsieh | |
| 2010/0047239 A1 | 2/2010 | Wu | |
| 2010/0221179 A1 | 9/2010 | Hsieh | |

FOREIGN PATENT DOCUMENTS

| | | |
|---|---|---|
| EP | 0267611 | 5/1993 |
| EP | 0659766 | * 6/1995 |
| WO | 2010087972 | 8/2010 |

OTHER PUBLICATIONS

Pascual, V. et al: "Role of interleukin-1 (IL-1) in the pathogenesis of systemic onset juvenile idiopathic arthritis and clinical response to IL-1 blockade," The Journal of Experimental Medicine (2005), vol. 201, No. 9:1479-1486.

Buchan, G. et al: "Interleukin-1 and tumour necrosis factor mRNA expression in rheumatoid arthritis: prolonged production of IL-1alpha," Clin. Exp. Immunol. (1988), vol. 73:449-455.

Hata, H. et al: "Distinct contribution of IL-6, TNF-alpha, IL-1, and IL-10 to T cell-mediated spontaneous autoimmune arthritis in mice," The Journal of Clinical Investigation (2004), vol. 114, No. 4: 582-588.

Chen, Z. et al: "Effects of interleukinlalpha, interleukin-1 receptor antagonist, and neutralizing antibody on proinflammatory cytokine expression by human squamous cell carcinoma lines," Cancer Research (1998), vol. 58:3668-367.

Kaji, Mitsuhito et al, E-selectin expression induced by pancreas-carcinoma-derived interleukin-1alpha results in enhanced adhesion of pancreas-carcinoma cells to endothelial cells, Intl Journal of Cancer, 1995, vol. 60, Issue 5:712-717.

Jefferis, Roy: "Antibody therapeutics: isotype and glycoform selection," Expert Opin. Biol. Ther. (2007) 7 (9)1401-1413.

Salfeld, J.G.: "Isotype selection in antibody engineering," Nature Biotechnology (2007), vol. 25, No. 12:1369-1372.

Kleiman, et al: "Invasion assays," Current Protocols in Cell Biology, 2001, 12.2.1-12.2.5.

Dekker, S.K. et al: "Characterization of interleukin-1alpha-induced melanoma cell motility: inhibition by type I and type II receptor-blocking monoclonal antibodies," Melanoma Research, 1997, vol. 7:223-230.

Lewis, Anne M. et al: "Interleukin-I and cancer progression: the emerging role of interleukin-l receptor antagonist as a novel therapeutic agent in cancer treatment," Journal of Translational Medicine, 2006, vol. 4:1-12.

Li, X. et al: "Interleukin-1alpha up-regulation in vivo by a potent carcinogen 7, 12-Dimethylbenz(a)anthracene (DMB) and control of DMBA-induced inflammatory responses," Cancer Res, 2002, vol. 62:417-423.

Sawai, H. et al: "Interleukin-1alpha enhances the aggressive behavior of pancreatic cancer cells by regulating the alpha 6 beta I-integrin and urokinase plasminogen activator receptor expression," MC Cell Biology, 2006:1-13.

Nozaki, S. et al: "Cancer Cell-Derived Interleukin 1alpha contributes to autocrine and paracrine induction of pro-metastatic genes in breast cancer," Biochemical and Biophysical Research Communications, 2000, vol. 275:60-62.

Voronov, E. et al: "IL-1 is required for tumor invasiveness and angiogenesis," PNAS, 2003, vol. 100, No. 5:2645-2650.

(Continued)

Primary Examiner — Elly-Gerald Stoica

(74) Attorney, Agent, or Firm — Stanley A. Kim, Esq.

(57) ABSTRACT

The invention is based on the discovery that interleukin-1 alpha (IL-1alpha) is expressed on the proinflammatory CD14+CD16+ monocyte subset. Importantly, since IL-1alpha appears to be almost exclusively expressed on this monocyte subset and not other leukocytes, it represents an ideal marker for targeting the CD14+CD16+ monocyte subset. The effectiveness of an agent that depletes such pathogenic cells or modulates IL-1alpha function on such cells type can be monitored by assessing CD14+CD16+ monocyte levels or functionality.

14 Claims, No Drawings

(56) References Cited

OTHER PUBLICATIONS

Uefuji, K. et al "Increased expression of interleukin-1alpha and cyclooxygenase-2 in human gastric cancer: a possible role in tumor progression," 2005, Anticancer Research, vol. 25:3225-3230.

Fukumoto, Y. et al., Inflammatory Cytokines Cause Coronary Arteriosclerosis-Like Changes and Alterations in the Smooth-Muscle Phenotypes in Pigs, Journal of Cardiovascular Pharmacology, 1997, vol. 29:222-231.

Chamberlain, R.S. et al., Innovations and strategies for the development of anticancer vaccines, Exp. Opin. Pharmacother., 2000, vol. 1(4)603-614.

Barkley, D.E.H. et al: "Cells with dendritic morphology and bright interleukin-1alpha staining circulate in the blood of patients with rheumatoid arthritis," Clin.Exp.Immmunol., 1990, vol. 80:25-31.

Yanni, G. et al: "Intramuscular gold decreases cytokine expression and macrophage numbers in the rheumatoid synovial membrane," Annals of the Rheumatic Diseases, 1994, vol. 53:315-322.

Shreeniwas, R. et al: "Hypoxia-mediated induction of endothelial cell interleukin-1alpha: an autocrine mechanism promoting expression of leukocyte adhesion molecules on the vessel surface," 1992, J. Clin. Invest., vol. 90:2333-2339.

Zhu, Y. et al., "The Clinical study about interleukin-1 and tumor necrosis factor Alpha in hepatocirrhosis," Chinese Journal of Clinical Hepatology, 2001, vol. 17, Issue 4: 233-234.

Skrzeczynska, J. et al., "CD14+CD16+ Monocytes in the Course of Sepsis in Neonates and Small Children: Monitoring and Functional Studies," Scandinavian Journal of Immunology, 2002, vol. 55:629-638.

Mizutani, H.: "Endogenous neutralizing anti-Il-1alpha antibodies in inflammatory skin diseases: possible natural inhibitor for over expressed epidermal IL-1," 1999, Journal of Dermatological Science, vol. 20:63-71.

\* cited by examiner

SEQUENCE LISTING

```
<160> NUMBER OF SEQ ID NOS: 4

<210> SEQ ID NO 1
<211> LENGTH: 471
<212> TYPE: PRT
<213> ORGANISM: Homo sapiens

<400> SEQUENCE: 1

Met Glu Phe Gly Leu Ser Trp Val Phe Leu Val Ala Leu Leu Arg Gly
1               5                   10                  15

Val Gln Cys Gln Val Gln Leu Val Glu Ser Gly Gly Gly Val Val Gln
            20                  25                  30

Pro Gly Arg Ser Leu Arg Leu Ser Cys Thr Ala Ser Gly Phe Thr Phe
        35                  40                  45

Ser Met Phe Gly Val His Trp Val Arg Gln Ala Pro Gly Lys Gly Leu
    50                  55                  60

Glu Trp Val Ala Ala Val Ser Tyr Asp Gly Ser Asn Lys Tyr Tyr Ala
65                  70                  75                  80

Glu Ser Val Lys Gly Arg Phe Thr Ile Ser Arg Asp Asn Ser Lys Asn
                85                  90                  95

Ile Leu Phe Leu Gln Met Asp Ser Leu Arg Leu Glu Asp Thr Ala Val
            100                 105                 110

Tyr Tyr Cys Ala Arg Gly Arg Pro Lys Val Val Ile Pro Ala Pro Leu
        115                 120                 125

Ala His Trp Gly Gln Gly Thr Leu Val Thr Phe Ser Ser Ala Ser Thr
    130                 135                 140

Lys Gly Pro Ser Val Phe Pro Leu Ala Pro Ser Ser Lys Ser Thr Ser
145                 150                 155                 160

Gly Gly Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Ser Leu Gly Thr Gln Thr Tyr Ile Cys
    210                 215                 220
```

```
Asn Val Asn His Lys Pro Ser Asn Thr Lys Val Asp Lys Lys Val Glu
225                 230                 235                 240

Pro Lys Ser Cys Asp Lys Thr His Thr Cys Pro Pro Cys Pro Ala Pro
                245                 250                 255

Glu Leu Leu Gly Gly Pro Ser Val Phe Leu Phe Pro Pro Lys Pro Lys
            260                 265                 270

Asp Thr Leu Met Ile Ser Arg Thr Pro Glu Val Thr Cys Val Val Val
        275                 280                 285

Asp Val Ser His Glu Asp Pro Glu Val Lys Phe Asn Trp Tyr Val Asp
        290                 295                 300

Gly Val Glu Val His Asn Ala Lys Thr Lys Pro Arg Glu Glu Gln Tyr
305                 310                 315                 320

Asn Ser Thr Tyr Arg Val Val Ser Val Leu Thr Val Leu His Gln Asp
                325                 330                 335

Trp Leu Asn Gly Lys Glu Tyr Lys Cys Lys Val Ser Asn Lys Ala Leu
            340                 345                 350

Pro Ala Pro Ile Glu Lys Thr Ile Ser Lys Ala Lys Gly Gln Pro Arg
        355                 360                 365

Glu Pro Gln Val Tyr Thr Leu Pro Pro Ser Arg Asp Glu Leu Thr Lys
        370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415

Thr Thr Pro Pro Val Leu Asp Ser Asp Gly Ser Phe Phe Leu Tyr Ser
            420                 425                 430

Lys Leu Thr Val Asp Lys Ser Arg Trp Gln Gln Gly Asn Val Phe Ser
        435                 440                 445

Cys Ser Val Met His Glu Ala Leu His Asn His Tyr Thr Gln Lys Ser
        450                 455                 460

Leu Ser Leu Ser Pro Gly Lys
465                 470

<210> SEQ ID NO 2
<211> LENGTH: 234
<212> TYPE: PRT
<213> ORGANISM: Homo sapiens

<400> SEQUENCE: 2

Met Asp Met Arg Val Pro Ala Gln Leu Leu Gly Leu Leu Leu Leu Trp
1               5                   10                  15

Phe Pro Gly Ser Arg Cys Asp Ile Gln Met Thr Gln Ser Pro Ser Ser
                20                  25                  30

Val Ser Ala Ser Val Gly Asp Arg Val Thr Ile Thr Cys Arg Ala Ser
            35                  40                  45

Gln Gly Ile Ser Ser Trp Leu Ala Trp Tyr Gln Gln Lys Pro Gly Lys
        50                  55                  60

Ala Pro Lys Leu Leu Ile Tyr Glu Ala Ser Asn Leu Glu Thr Gly Val
65                  70                  75                  80

Pro Ser Arg Phe Ser Gly Ser Gly Ser Gly Asp Phe Thr Leu Thr
                85                  90                  95

Ile Ser Ser Leu Gln Pro Glu Asp Phe Ala Thr Tyr Tyr Cys Gln Gln
                100                 105                 110

Thr Ser Ser Phe Leu Leu Ser Phe Gly Gly Gly Thr Lys Val Glu His
            115                 120                 125
```

```
Thr Val Ala Ala Pro Ser Val Phe Ile Phe Pro Ser Asp Glu Gln
130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
                180                 185                 190

Tyr Ser Leu Ser Ser Thr Leu Thr Leu Ser Lys Ala Asp Tyr Glu Lys
            195                 200                 205

His Lys Val Tyr Ala Cys Glu Val Thr His Gln Gly Leu Ser Ser Pro
        210                 215                 220

Val Thr Lys Ser Phe Asn Arg Gly Glu Cys
225                 230

<210> SEQ ID NO 3
<211> LENGTH: 471
<212> TYPE: PRT
<213> ORGANISM: Homo sapiens

<400> SEQUENCE: 3

Met Glu Phe Gly Leu Ser Trp Val Phe Leu Val Ala Leu Leu Arg Gly
1               5                   10                  15

Val Gln Cys Gln Val Gln Leu Val Glu Ser Gly Gly Gly Val Val Gln
            20                  25                  30

Pro Gly Arg Ser Leu Arg Leu Ser Cys Thr Ala Ser Gly Phe Thr Phe
        35                  40                  45

Ser Met Phe Gly Val His Trp Val Arg Gln Ala Pro Gly Lys Gly Leu
    50                  55                  60

Glu Trp Val Ala Ala Val Ser Tyr Asp Gly Ser Asn Lys Tyr Tyr Ala
65                  70                  75                  80

Glu Ser Val Lys Gly Arg Phe Thr Ile Ser Arg Asp Asn Ser Lys Asn
                85                  90                  95

Ile Leu Phe Leu Gln Met Asp Ser Leu Arg Leu Glu Asp Thr Ala Val
            100                 105                 110

Tyr Tyr Cys Ala Arg Gly Arg Pro Lys Val Val Ile Pro Ala Pro Leu
        115                 120                 125

Ala His Trp Gly Gln Gly Thr Leu Val Thr Phe Ser Ser Ala Ser Thr
    130                 135                 140

Lys Gly Pro Ser Val Phe Pro Leu Ala Pro Ser Ser Lys Ser Thr Ser
145                 150                 155                 160

Gly Gly Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Ser Leu Gly Thr Gln Thr Tyr Ile Cys
    210                 215                 220

Asn Val Asn His Lys Pro Ser Asn Thr Lys Val Asp Lys Arg Val Glu
225                 230                 235                 240

Pro Lys Ser Cys Asp Lys Thr His Thr Cys Pro Pro Cys Pro Ala Pro
                245                 250                 255

Glu Leu Leu Gly Gly Pro Ser Val Phe Leu Phe Pro Lys Pro Lys
            260                 265                 270
```

```
Asp Thr Leu Met Ile Ser Arg Thr Pro Glu Val Thr Cys Val Val Val
            275                 280                 285

Asp Val Ser His Glu Asp Pro Glu Val Lys Phe Asn Trp Tyr Val Asp
    290                 295                 300

Gly Val Glu Val His Asn Ala Lys Thr Lys Pro Arg Glu Glu Gln Tyr
305                 310                 315                 320

Asn Ser Thr Tyr Arg Val Val Ser Val Leu Thr Val Leu His Gln Asp
                325                 330                 335

Trp Leu Asn Gly Lys Glu Tyr Lys Cys Lys Val Ser Asn Lys Ala Leu
                340                 345                 350

Pro Ala Pro Ile Glu Lys Thr Ile Ser Lys Ala Lys Gly Gln Pro Arg
            355                 360                 365

Glu Pro Gln Val Tyr Thr Leu Pro Pro Ser Arg Glu Glu Met Thr Lys
    370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415

Thr Thr Pro Pro Val Leu Asp Ser Asp Gly Ser Phe Phe Leu Tyr Ser
            420                 425                 430

Lys Leu Thr Val Asp Lys Ser Arg Trp Gln Gln Gly Asn Val Phe Ser
    435                 440                 445

Cys Ser Val Met His Glu Ala Leu His Asn His Tyr Thr Gln Lys Ser
450                 455                 460

Leu Ser Leu Ser Pro Gly Lys
465                 470

<210> SEQ ID NO 4
<211> LENGTH: 236
<212> TYPE: PRT
<213> ORGANISM: Homo sapiens

<400> SEQUENCE: 4

Met Asp Met Arg Val Pro Ala Gln Leu Leu Gly Leu Leu Leu Leu Trp
1               5                   10                  15

Phe Pro Gly Ser Arg Cys Asp Ile Gln Met Thr Gln Ser Pro Ser Ser
                20                  25                  30

Val Ser Ala Ser Val Gly Asp Arg Val Thr Ile Thr Cys Arg Ala Ser
            35                  40                  45

Gln Gly Ile Ser Ser Trp Leu Ala Trp Tyr Gln Gln Lys Pro Gly Lys
    50                  55                  60

Ala Pro Lys Leu Leu Ile Tyr Glu Ala Ser Asn Leu Glu Thr Gly Val
65                  70                  75                  80

Pro Ser Arg Phe Ser Gly Ser Gly Ser Gly Ser Asp Phe Thr Leu Thr
                85                  90                  95

Ile Ser Ser Leu Gln Pro Glu Asp Phe Ala Thr Tyr Tyr Cys Gln Gln
            100                 105                 110

Thr Ser Ser Phe Leu Leu Ser Phe Gly Gly Gly Thr Lys Val Glu His
    115                 120                 125

Lys Arg Thr Val Ala Ala Pro Ser Val Phe Ile Phe Pro Pro Ser Asp
130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175
```

-continued

```
Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235
```

MODULATION OF PATHOGENIC CD14+/CD16+ MONOCYTES

CROSS-REFERENCE TO RELATED APPLICATIONS

The present application is a continuation of U.S. nonprovisional patent application Ser. No. 12/559,019 filed on Sep. 14, 2009, which claims the priority of U.S. provisional patent application Ser. No. 61/096,563 filed on Sep. 12, 2008.

STATEMENT AS TO FEDERALLY SPONSORED RESEARCH

Not applicable.

FIELD OF THE INVENTION

The invention relates generally to the fields of immunology, leukocyte biology, inflammation, cancer, vascular disorders, and medicine. More particularly, the invention relates to methods of determining treatment options, methods of assessing treatment efficacy, and methods for targeting disease-associated leukocytes without causing significant morbidity or generalized immunosuppression.

BACKGROUND

Leukocytes, or white blood cells, are cells of the immune system that protect the body against infectious disease and toxins. There are several different and functionally diverse kinds of leukocytes in humans, all however are derived from a common pluripotent bone marrow-derived stem cell. In a healthy person there are about $8 \times 10^6$ leukocytes per milliliter of blood. These leukocytes are comprised of basophils, lymphocytes, neutrophils, eosinophils, macrophages and monocytes. The monocyte fraction accounts only for about 2-8% of all leukocytes.

The macrophage was first observed by physicians during the mid-nineteenth century, when these cells were described in battlefield wounds and in association with areas of chronic inflammation. Extensive study of these cells since has revealed that the monocyte-macrophage system plays several crucial functions: in tissue maintenance and repair; immune regulation; and in control and elimination of pathogens.

Monocytes are only temporary residents in the blood. After development in the bone marrow, monocytes circulate in the bloodstream where they have a half-life of a few days. During an acute inflammatory response, the half-life may be only a few hours. Egress of monocytes from the blood into tissues is associated with an increase in cell size together with a larger, lighter-staining nucleus, indicating intense RNA expression. These tissue-infiltrated cells are termed macrophages (or histiocytes). These cells are phagocytic and mobile.

When monocytes take up residence in various tissues they may persist there for years. In the spleen, macrophages are involved in recycling old red blood cells; in the skin (Langerhans cells), they are involved in keratinization of the epidermis; in the liver (Kupfer cells), they manage degradation of toxins; in the intima of the artery (foam cells), they are involved in the formation of atherosclerotic plaques; in the joint, they differentiate into cells (type A synoviocytes) that are involved in maintenance of the joint; in lymph nodes, they function as antigen presenting cells (dendritic cells), stimulating adaptive immune responses; in bone, they regulate resorption of bone mass (osteoclasts); while in the central nervous system (glial cells), they act as sentinel cells and are involved in neuroendocrine homeostasis. Monocytes and the cells that they differentiate were once commonly referred to as the reticuloendothelial system. While no longer popularly referred to as such, this nomenclature addressed the multiple roles of monocytes in the homeostasis of tissues and organ systems.

In order for monocytes to perform their myriad functions in tissues, they first must exit the blood vessel and enter tissue. To accomplish this, monocytes, once activated, adhere to the endothelial cells of the blood vessel wall and extravasate, or penetrate, the cell matrix that forms the vessel wall. This extravasation process is not unique to monocytes. The molecular mechanism of adherence involves the adhesion molecules CD11a, CD11b, CD11c/CD18, common to virtually all monocytes, as well as lymphocytes and neutrophils. Since extravasation of leukocytes into tissues is the first step in many disease processes, attempts have been made to block this process with antibodies. Extreme care, however, must be taken not to effect a generalized blockade of this process. The human genetic disease known as Leukocyte adhesion deficiency (LAD), a defect of the CD11/CD18 system, results in severe immunosuppression. Individuals with LAD die from opportunistic infections if left unprotected from pathogens. Consequently only a very selective blockade of this process is acceptable. One such treatment involves the use of an antibody Efalizumab, which targets CD11c, which is expressed as CD11c/CD18 on certain leukocyte subsets, such a T lymphocytes. However, no means for selectively blocking monocyte function has been devised.

As distinguished from other leukocytes, monocytes represent a unique cellular compartment. Yet monocytes themselves are a functionally heterogeneous population of cells. In humans, these populations may be generally divided into two groups based on expression of cell surface markers: (1) the major population defined as CD14 high expressing (CD14++) and (2) the minor population defined as CD14 and CD16 co-expressing (CD14+CD16+). The latter is known as a proinflammatory subset of monocytes and is associated with numerous inflammation-associated diseases including atherosclerosis, cancer, rheumatoid arthritis, and Alzheimer's disease.

Therapeutic strategies involving leukocytopheresis to remove pro-inflammatory CD14+CD16+ monocytes from patients have been attempted. For example, extracorporeal elimination of CD14+CD16+ monocytes was successful in treating ulcerative colitis (Kanai et al. Inflamm. Bowel Dis. 2007 March; 13(3):284-90). This approach, however, resulted in significant morbidity and risk to the patient and is not suitable for treatment of chronic illness. Moreover, leukocytophoresis is not highly selective for CD14+CD16+ monocytes but rather depletes most monocyte populations. Therefore, leukocytophoresis is not suitable for treatment of diseases where sustained, long-term depletion is necessary, since this is expected to cause dangerous immunosuppression. Rather a highly selective means of targeting CD14+ CD16+ is necessary.

A preferred approach would be to selectively target the CD14+CD16+ proinflammatory monocyte subset with an agent that specifically downregulates that subset's function. Heretofore, no practical means to precisely target these cells has been identified. Although these cells are characterized by expression of CD14 and CD16 surface proteins, these are not appropriate for targeting therapy. CD14 would not be an appropriate target because it is expressed by all monocytes as well as other cells populations, such as neutrophils. Modulating function of the entire population of CD14-expressing cells would result in unacceptable risk of severe immunosuppression. Targeting CD16 (FcgRIII) would also not be appropriate because, in addition to expression on monocytes, it is expressed on a number of other crucial immune cells including B and T lymphocytes. Accordingly, a good marker for targeting those CD14+CD16+ monocytes has been lacking.

SUMMARY

The invention is based on the discovery that interleukin-1 alpha (IL-1alpha) is expressed on the proinflammatory, disease-associated CD14+CD16+ monocyte subset in humans. Importantly, because IL-1alpha appears to be almost exclusively expressed on this monocyte subset, it represents an ideal marker for targeting the CD14+CD16+ monocyte subset. Moreover, this discovery allows the effectiveness of an agent that depletes such pathogenic cells or modulates IL-1alpha function on such cell types to be monitored by assessing CD14+CD16+ monocyte levels or functionality.

Accordingly, the invention features a method including the steps of: (a) administering an agent that modulates the function or expression of IL-1alpha to a human subject; and (b) determining whether such administration modulates the amount or function of CD14+/CD16+ in the subject. The method might also include a step of first determining whether the subject has CD14+/CD16+ monocytes in an amount that contributes to a disease or pathologic disorder and/or whether the functional attributes of the subject's CD14+/CD16+ monocytes contributes to a disease or pathologic disorder.

The invention also features a method including the steps of: (a) determining whether a human subject has CD14+/CD16+ monocytes in an amount that contributes to a disease or pathologic disorder; and (b) administering an agent that modulates the function or expression of IL-1alpha to a human subject. This method can also include the step (c) of determining whether such administration modulates the amount of CD14+ CD16+ monocytes in the subject.

Also within the invention is a method including the steps of: (a) determining whether the functional attributes of a human subject's CD14+/CD16+ monocytes contributes to a disease or pathologic disorder; and (b) administering an agent that modulates the function or expression of IL-1alpha to a human subject. This method can also include the step (c) of determining whether such administration modulates the function of CD14+CD16+ monocytes in the subject.

In these methods, the agent that modulates the function or expression of IL-1alpha can be one that interferes with IL-1alpha binding to an IL-1alpha receptor or one that modulates the level of transcription or translation of a nucleic acid encoding IL-1alpha. For example, the agent can be an antibody (Ab) that specifically binds IL-1alpha or an IL-1alpha receptor. The Ab can be one that when administered to the subject reduces the amount or function of CD14+CD16+ monocytes in the subject.

The Ab can be a monoclonal antibody (mAb), e.g., a mAb that specifically binds IL-1alpha. The antibody can be a human Ab such as a monoclonal human $IgG_1$ that specifically binds IL-1alpha (e.g., one that has a heavy chain including the amino acid sequence of SEQ ID NO:1 and a light chain including the amino acid sequence of SEQ ID NO:2; or one that has a heavy chain including the amino acid sequence of SEQ ID NO:3 and a light chain including the amino acid sequence of SEQ ID NO:4).

In the methods, the agent that modulates the function or expression of IL-1alpha can also be a vaccine that increases the concentration of Abs that specifically bind IL-1alpha or an IL-1alpha receptor in the subject, or a nucleic acid that reduces or modulates IL-1alpha expression in the subject.

The human subject can be a person having a pathology associated with aberrant function or levels of CD14+CD16+ monocytes. For example, the pathology can be an inflammatory condition or an autoimmune condition such as cancer, atherosclerosis, rheumatoid arthritis, or inflammatory bowel disease. The human subject can also be a person having an abnormally high level of peripheral blood that are CD14+ CD16+ monocytes leukocytes (e.g., at least 1.5% of total white blood cells in a complete blood count with differential) before administration of the agent or a person having normal or less than normal levels of peripheral blood leukocytes that are CD14+CD16+ monocytes (e.g., less than 1.5% of total white blood cells in a complete blood count with differential) after administration of the agent. The human subject can also be a person having an abnormally high level of peripheral blood monocytes that are CD14+CD16+ monocytes (e.g., at least 10% of monocytes are CD14+CD16+) before administration of the agent.

In these methods, the step of determining whether such administration modulates the amount or function of CD14+ CD16+ monocytes in the subject can include determining the subject's amount (e.g., number, percent of total white blood cells in a complete blood count with differential, concentration, and/or ratio to other blood cells such as CD14++ monocytes) of CD14+CD16+ monocytes before and after administration and/or assessing the function of the subject's CD14+ CD16+ monocytes (e.g., assessing binding to endothelial cells such as human umbilical vein endothelial cells (HUVEC)) before and after administration.

Unless otherwise defined, all technical terms used herein have the same meaning as commonly understood by one of ordinary skill in the art to which this invention belongs. Commonly understood definitions of biological terms can be found in Rieger et al., Glossary of Genetics: Classical and Molecular, 5th edition, Springer-Verlag: New York, 1991; and Lewin, Genes V, Oxford University Press: New York, 1994.

By the term "antibody" is meant an immunoglobulin as well as any portion or fragment of an immunoglobulin whether made by enzymatic digestion of intact immunoglobulin or by techniques in molecular biology. The term also refers to a mixture containing an immunoglobulin (or portion or fragment thereof) such as an antiserum.

As used herein, the term "human antibody" or "human Ab" generally refers to an immunoglobulin (Ig) which is substantially non-immunogenic in humans.

The term "specifically binds", as used herein, when referring to a polypeptide (including Abs) or receptor, refers to a binding reaction which is determinative of the presence of the protein or polypeptide or receptor in a heterogeneous population of proteins and other biologics. Thus, under designated conditions (e.g. immunoassay conditions in the case of an antibody), the specified ligand or Ab binds to its particular "target" and does not bind in a significant amount to other proteins present in the sample or to other proteins to which the ligand or Ab may come in contact with in an organism. Generally, a first molecule that "specifically binds" a second molecule has an equilibrium affinity constant greater than about $10^5$ (e.g., $10^6$, $10^7$, $10^8$, $10^9$, $10^{10}$, $10^{11}$, and $10^{12}$ or more) liters/mole for that second molecule.

When referring to a protein molecule such as an Ab, "purified" means separated from components that naturally accompany such molecules. Typically, an Ab or protein is purified when it is at least about 10% (e.g., 9%, 10%, 20%, 30% 40%, 50%, 60%, 70%, 80%, 90%, 95%, 98%, 99%, 99.9%, and 100%), by weight, free from the non-Ab proteins or other naturally-occurring organic molecules with which it is naturally associated. Purity can be measured by any appropriate method, e.g., column chromatography, polyacrylamide gel electrophoresis, HPLC analysis, or other suitable method. A chemically-synthesized protein or other recombinant protein produced in a cell type other than the cell type in which it naturally occurs is "purified."

Although methods and materials similar or equivalent to those described herein can be used in the practice or testing of the present invention, suitable methods and materials are described below. All publications, patent applications, patents, and other references mentioned herein are incorporated by reference in their entirety. In the case of conflict, the present specification, including definitions will control. In addition, the particular embodiments discussed below are illustrative only and not intended to be limiting.

DETAILED DESCRIPTION

The invention encompasses methods for assessing whether administration of an IL-1alpha targeting agent to a human subject modulates the function or amount of CD14+CD16+ monocytes in the subject. The below described preferred embodiments illustrate adaptation of these methods. Nonetheless, from the description of these embodiments, other aspects of the invention can be made and/or practiced based on the description provided below.

General Methods

Methods involving conventional immunological and molecular biological techniques are described herein Immunological methods (for example, assays for detection and localization of antigen-Ab complexes, immunoprecipitation, immunoblotting, and the like) are generally known in the art and described in methodology treatises such as Current Protocols in Immunology, Coligan et al., ed., John Wiley & Sons, New York. Techniques of molecular biology are described in detail in treatises such as Molecular Cloning: A Laboratory Manual, 2nd ed., vol. 1-3, Sambrook et al., ed., Cold Spring Harbor Laboratory Press, Cold Spring Harbor, N.Y., 2001; and Current Protocols in Molecular Biology, Ausubel et al., ed., Greene Publishing and Wiley-Interscience, New York. Ab methods are described in Handbook of Therapeutic Antibodies, Dubel, S., ed., Wiley-VCH, 2007. Methods of blood cell analysis are described in Flow Cytometry, David Keren, American Society for Clinical Pathology; 4th edition, 2007 and Lichtman et al., Williams Hematology, McGraw-Hill Professional; 7th edition, 2005.

Agents that Modulate the Function and/or Expression of IL-1alpha

Various methods of the invention feature a step of administering to a human subject an agent that modulates the function or expression of IL-1alpha. Any suitable agent that modulates the function or expression of IL-1alpha might be used. The agent, for example, can be one that binds IL-1alpha, one that interferes with IL-1alpha binding to an IL-1alpha receptor, or one that modulates the level of transcription or translation of a nucleic acid encoding IL-1alpha. Numerous such agents are known or can be made by a skilled artisan using the teachings herein or the knowledge in the art. These include antibodies that specifically bind IL-1alpha or an IL-1alpha receptor (such that it blocks binding to IL-1alpha), vaccines that increase the concentration of such antibodies in a subject, IL-1alpha binding proteins such as IL-1alpha receptors and variants (e.g., fragments or amino acid substitution mutants) thereof, nucleic acids which bind IL-1alpha (e.g., aptamers), small organic molecules which specifically bind IL-1alpha, nucleic acids that reduce or modulate IL-1alpha expression, and combinations of two or more (e.g., 2, 3, 4, 5 or more) of the foregoing.

Antibodies

Antibodies that are useful in the methods of the invention include those, that when administered to a subject, modulate (e.g., reduce) the amount or function of CD14+CD16+ monocytes in the subject. Because CD14+CD16+ monocytes also express IL-1alpha, Abs that specifically bind IL-1alpha or an IL-1alpha receptor can be used to modulate the function or amount of such monocytes. Anti-IL-1alpha or anti-IL-1alpha receptor Abs can be polyclonal or monoclonal. To prevent undesirable reactions, Abs for use in methods of the invention are preferably humanized or more preferably human.

The methods of the invention preferably use a human mAb that includes (i) an antigen-binding variable region that exhibits very high binding affinity for human IL-1alpha and (ii) a constant region that is effective at both activating the complement system though C1q binding and binding to several different Fc receptors. The human Ab is preferably an IgG1. The Ka of the antibody is preferably at least $1\times10^9\,M^{-1}$ or greater (e.g., greater than $1\times10^{10}\,M^{-1}$). The human Ab can include a heavy chain including the amino acid sequence of SEQ ID NO:1 and a light chain including the amino acid sequence of SEQ ID NO:2; or one that has a heavy chain including the amino acid sequence of SEQ ID NO:3 and a light chain including the amino acid sequence of SEQ ID NO:4).

Although generally less preferred, chimeric anti-IL-1alpha mAbs (e.g., "humanized" mAbs), which are antigen-binding molecules having different portions derived from different animal species (e.g., variable region of a mouse Ig fused to the constant region of a human Ig), might also be used in the invention. Such chimeric antibodies can be prepared by methods known in the art. E.g., Morrison et al., Proc. Nat'l. Acad. Sci. USA, 81:6851, 1984; Neuberger et al., Nature, 312:604, 1984; Takeda et al., Nature, 314:452, 1984. Similarly, antibodies can be humanized by methods known in the art. For example, monoclonal antibodies with a desired binding specificity can be commercially humanized or as described in U.S. Pat. No. 5,693,762; 5,530,101; or 5,585,089.

Preferably, to ensure that high titers of Ab can be administered to a subject with minimal adverse effects, the mAb compositions which may be used in the invention are at least 0.5, 1, 2, 3, 4, 5, 6, 7, 8, 9, 10, 11, 12, 13, 14, 15, 20, 25, 30, 35, 40, 45, 50, 60, 70, 80, 90, 95, 96, 97, 98, 99, 99.9 or more percent by weight pure (excluding any excipients). The Ab compositions might include only a single type of mAb (i.e., one produced from a single clonal B lymphocyte line) or might include a mixture of two or more (e.g., 2, 3, 4, 5, 6, 7, 8, 9, 10 or more) different types of mAbs.

To modify or enhance their function, the Abs might be conjugated another molecule such as a cytotoxin. An IL-1alpha-specific Ab might be conjugated with one or more cytotoxins to more effectively kill cells expressing IL-1alpha. Cytotoxins for use in the invention can be any cytotoxic agent (e.g., a molecule that can kill a cell after contacting it) that can be conjugated to a mAb. Examples of cytotoxins include, without limitation, radionuclides (e.g., $^{35}S$, $^{14}C$, $^{32}P$, $^{125}I$, $^{131}I$, $^{90}Y$, $^{89}Zr$, $^{201}Tl$, $^{186}Re$, $^{188}Re$, $^{57}Cu$, $^{213}Bi$, and $^{211}At$), conjugated radionuclides, and chemotherapeutic agents. Further examples of cytotoxins include, but are not limited to, antimetabolites (e.g., 5-fluorouricil (5-FU), methotrexate (MTX), fludarabine, etc.), anti-microtubule agents (e.g., vincristine, vinblastine, colchicine, taxanes (such as paclitaxel and docetaxel), etc.), alkylating agents (e.g., cyclophasphamide, melphalan, bischloroethylnitrosurea (BCNU), etc.), platinum agents (e.g., cisplatin (also termed cDDP), carboplatin, oxaliplatin, JM-216, CI-973, etc.), anthracyclines (e.g., doxorubicin, daunorubicin, etc.), antibiotic agents (e.g., mitomycin-C), topoisomerase inhibitors (e.g., etoposide, tenoposide, and camptothecins), or other cytotoxic agents such as ricin, diptheria toxin (DT), Pseudomonas exotoxin (PE) A, PE40, abrin, saporin, pokeweed viral protein, ethidium bromide, glucocorticoid, anthrax toxin and others. See, e.g., U.S. Pat. No. 5,932,188.

Vaccines

In the method, the agent that modulates (e.g., inhibits) the function or expression of IL-1alpha can also be a vaccine that increases the concentration of antibodies that specifically bind IL-1alpha in the subject. A suitable vaccine can include an immunogenic form of IL-1alpha in a pharmaceutically acceptable carrier. An adjuvant such as aluminum salts might be included as well. The immunogenic form of IL-1alpha might include the intact protein or peptide fragments of such protein. To enhance an immune response, the immunogenic form of IL-1alpha might be conjugated with a carrier protein such as keyhole limpet hemocyanin or pseudomonas exotoxin. Abs produced as a result of vaccine administration might be collected and used as described above.

IL-1alpha Modulating Proteins and Mimetics

Examples of proteins that modulate IL-1alpha expression and/or function by direct targeting include IL-1 receptors (IL-1Rs) such as IL-1RI, IL-1RII, and IL-1alpha-binding variants thereof (e.g., recombinant forms, fragments, mimetics, mutants, and conjugates thereof). Soluble forms of IL-1Rs are preferred for their ease of administration. Examples of proteins that can indirectly modulate IL-1alpha expression and/or function include proteins that can compete with monocyte-associated IL-1alpha for binding ligands such as IL-1Rs (e.g., those that do not transduce activating signals). These might include a modified non-activating IL-1alpha (including pro-IL-1alpha, membrane-associated IL-1alpha, and recombinant IL-1alpha), a modified non-activating IL-1beta (including pro-IL-1beta and mature IL-1beta), IL-1 receptor antagonist (IL-1Ra; including soluble IL-1Ra, icIL-1RaI, and icIL-1RaII), and variants thereof.

Protein (including Ab) variants can be generated through various techniques known in the art. For example, IL-1alpha, IL-1beta, IL-1Ra, and IL-1R variants can be made by mutagenesis, such as by introducing discrete point mutation(s), or by truncation. Mutation can give rise to a protein variant having substantially the same, or merely a subset of the functional activity of these proteins. Other protein variants that can be generated include those that are resistant to proteolytic cleavage, as for example, due to mutations which alter protease target sequences. Whether a change in the amino acid sequence of a peptide results in a protein variant having one or more functional activities of the native protein can be readily determined by testing the variant for a native protein functional activity. Non-peptide mimetic or chemically modified forms of the foregoing that modulate IL-1alpha expression or function can also be used. See, e.g., Freidinger et al. in Peptides: Chemistry and Biology, G. R. Marshall ed., ESCOM Publisher: Leiden, Netherlands, 1988); Ewenson et al. (1986) J. Med. Chem. 29:295; Ewenson et al. in Peptides: Structure and Function (Proceedings of the 9th American Peptide Symposium); Nagai et al. (1985) Tetrahedron Lett 26:647; Sato et al. (1986) J. Chem. Soc. Perkin. Trans. 1:1231); Gordon et al. (1985) Biochem. Biophys. Res. Commun 126:419; and Dann et al. (1986) Biochem. Biophys. Res. Commun 134:71). The foregoing may also be chemically modified to create derivatives by forming covalent or aggregate conjugates with other chemical moieties, such as glycosyl groups, lipids, phosphate, acetyl groups and the like. Covalent derivatives of proteins can be prepared by linking the chemical moieties to functional groups on amino acid side chains of the protein or at the N-terminus or at the C-terminus of the polypeptide. To modify or enhance their function, the foregoing agents might be conjugated another molecule such as one or more of the cytotoxins listed above.

IL-1alpha-Modulating Nucleic Acids

The agent that modulates expression/activity of IL-1alpha can also be a nucleic acid. For example, the nucleic acid can be a sense nucleic acid that encodes a IL-1alpha protein (e.g., introduction into a cell can increase the cells IL-1alpha activity). The nucleic acid can also be an antisense nucleic acid that hybridizes to mRNA encoding IL-1alpha to inhibit translation and decrease expression of the protein. Antisense nucleic acid molecules for use within the invention are those that specifically hybridize (e.g. bind) under cellular conditions to cellular mRNA and/or genomic DNA encoding a IL-1alpha protein in a manner that inhibits expression of the IL-1alpha protein, e.g., by inhibiting transcription and/or translation. The binding may be by conventional base pair complementarity, or, for example, in the case of binding to DNA duplexes, through specific interactions in the major groove of the double helix.

Antisense constructs can be delivered as an expression plasmid which, when transcribed in the cell, produces RNA which is complementary to at least a unique portion of the cellular mRNA which encodes a IL-1alpha protein. Alternatively, the antisense construct can take the form of an oligonucleotide probe generated ex vivo which, when introduced into a IL-1alpha protein expressing cell, causes inhibition of IL-1alpha protein expression by hybridizing with an mRNA and/or genomic sequences coding for IL-1alpha protein. Such oligonucleotide probes are preferably modified oligonucleotides that are resistant to endogenous nucleases, e.g., exonucleases and/or endonucleases, and are therefore stable in vivo. Exemplary nucleic acid molecules for use as antisense oligonucleotides are phosphoramidate, phosphothioate and methylphosphonate analogs of DNA (see, e.g., U.S. Pat. Nos. 5,176,996; 5,264,564; and 5,256,775).

Nucleic acid molecules can be delivered into cells that express IL-1alpha in vivo. A number of methods have been developed for delivering DNA or RNA into cells. For instance, such molecules can be introduced directly into a target site by such standard techniques as electroporation, liposome-mediated transfection, CaCl-mediated transfection, or the use of a gene gun. Alternatively, modified antisense molecules, designed to target the desired cells (e.g., antisense linked to peptides or antibodies that specifically bind receptors or antigens expressed on the target cell surface) can be used. Because it is often difficult to achieve intracellular concentrations of the antisense sufficient to suppress translation of endogenous mRNAs, a preferred approach utilizes a recombinant DNA construct in which the antisense oligonucleotide is placed under the control of a strong promoter (e.g., the CMV promoter). The use of such a construct to transform cells will result in the transcription of sufficient amounts of single stranded RNAs that will form complementary base pairs with the endogenous IL-1alpha transcripts and thereby prevent translation of IL-1alpha mRNA.

Ribozyme molecules designed to catalytically cleave IL-1alpha mRNA transcripts can also be used to prevent translation of IL-1alpha mRNA and expression of IL-1alpha protein (see, e.g., PCT Publication No. WO 90/11364, published Oct. 4, 1990; Sarver et al., Science 247:1222-1225, 1990 and U.S. Pat. No. 5,093,246). Preferably the ribozyme is engineered so that the cleavage recognition site is located near the 5' end of IL-1alpha mRNA; i.e., to increase efficiency and minimize the intracellular accumulation of non-functional mRNA transcripts. Ribozymes within the invention can be delivered to a cell using a vector.

Endogenous IL-1alpha gene expression can also be reduced by inactivating or "knocking out" the IL-1alpha gene or its promoter using targeted homologous recombination. See, e.g, Kempin et al., Nature 389: 802 (1997); Smithies et al., Nature 317:230-234, 1985; Thomas and Capecchi, Cell 51:503-512, 1987; and Thompson et al., Cell 5:313-321, 1989. For example, a mutant, non-functional IL-1alpha gene variant (or a completely unrelated DNA sequence) flanked by DNA homologous to the endogenous IL-1alpha gene (either the coding regions or regulatory regions of the IL-1alpha gene) can be used, with or without a selectable marker and/or a negative selectable marker, to transfect cells that express IL-1alpha protein in vivo.

Alternatively, endogenous IL-1alpha gene expression might be reduced by targeting deoxyribonucleotide sequences complementary to the regulatory region of the IL-1alpha gene (i.e., the IL-1alpha promoter and/or enhancers) to form triple helical structures that prevent transcription of the IL-1alpha gene in target cells. (See generally, Helene, C., Anticancer Drug Des. 6(6):569-84, 1991; Helene, C., et al., Ann. N.Y. Acad. Sci. 660:27-36, 1992; and Maher, L. J., Bioassays 14(12):807-15, 1992) Inhibition of IL-1alpha gene expression might also be performed using RNA interference (RNAi) techniques.

Nucleic Acids which Bind IL-1alpha (Aptamers)

Aptamers or nucleic acid species that have been engineered through repeated rounds of selection (e.g., by SELEX; systematic evolution of ligands by exponential enrichment) to bind to IL-1alpha might also be used in the invention to modulate the function of IL-1alpha. Methods of making and using aptamers against specific markers are described, e.g., in U.S. Pat. Nos. 5,670,637; 6,331,398; and 5,270,163; 5,567,588.

Small Molecules which Modulate IL-1alpha Expression/Function

Small molecules (generally organic) might also be modulate IL-1alpha expression or function. Known small molecules with anti-inflammatory action such as corticosteroids, cyclooxygenase inhibitors, linomide (roquinimex), thalidomide, pentoxifylline, and genistein might be used. Other molecules can be identified by screening libraries of small molecules to identify those that modulate (upregulate or downregulate) IL-1alpha expression in monocytes.

Determining Whether Administration of an Agent Modulates the Amount of CD14+CD16+ Monocytes in a Subject One method of the invention features a step of determining whether administration of an agent that modulates IL-1alpha expression and/or function modulates the amount of CD14+CD16+ monocytes in the subject can include determining the subject's amount (e.g., number, percent of leukocytes in a complete blood count with differential, concentration, ratio to other blood cells such as CD14++ monocytes) of CD14+CD16+ monocytes before and after administration. Determining the subject's amount of CD14+CD16+ monocytes before and after administration can be performed by any suitable method. For example, peripheral blood mononuclear cells (PBMCs) can be isolated from a human subject and then subjected to flow cytometry using antibodies specific for CD14 and CD16. Peripheral blood cells may also be centrifuged in order to concentrate the cells, and immunohistochemistry techniques used to identify and quantify the CD14+CD16+ population.

Determining Whether Administration of an Agent Modulates the Function of CD14+CD16+ Monocytes in a Subject One method of the invention features a step of determining whether administration of an IL-1alpha targeting agent modulates the function of CD14+CD16+ monocytes in the subject can include assessing the function of the subject's CD14+CD16+ monocytes before and after administration. Determining the subject's function of CD14+CD16+ monocytes before and after administration can be performed by any suitable method. For example, CD14+CD16+ monocytes can be isolated from peripheral blood mononuclear cells collected from a human subject. The isolated monocytes can then be subjected to an in vitro binding and transendothelial migration assay using human umbilical vein endothelial cells adhered to an artificial membrane substrate. See, e.g., Etingin et al. (1991) Proc. Nat'l. Acad. Sci. USA, 88:7200-7203.

A number of different assays may be performed to determine functional characteristics of the CD14+CD16+ monocytes. Leukocytes isolated from patients can be tested for their ability to induce pro-inflammatory cascade in vitro. The ability to stimulate synoviocytes to upregulate expression of MCP-1, or the ability to stimulate IL-2 production from the EL-4 T lymphocyte cell line are two such assays. Induction of these cytokines is dependent on CD14+CD16+ monocytes, thus these methods provide a means to determine the effectiveness of treatments aimed at reducing the pro-inflammatory activity of these cells in the peripheral blood.

To model the biology of circulating monocytes and their migration from blood into tissues, it is a standard art in the field to study this transmigration in vitro using established cell culture techniques coupled with the use of a polycarbonate filter assay (transwell assay). A source of primary endothelial cells (e.g., HUVEC) is seeded onto a polycarbonate filter (support matrix) and grown until forming a confluent monolayer. As such, this mimics the endothelium of blood vessel vasculature. Input cells of interest (leukocytes) are isolated from human blood and then applied to the upper chamber of the transwell device. Following an incubation period, the transwell insert is removed and transmigrated cells are collected from the bottom chamber for analysis. Flow cytometric analysis can be used to calculate the percentage of transmigrated cells and to determine their differentiation phenotype according to cell-surface protein markers. The in vitro migration of leukocytes across an endothelial barrier such as HUVEC can be sufficient to trigger cellular differentiation. Among leukocytes, monocyte transmigration through an endothelial cell monolayer has been shown to be sufficient to induce their differentiation into either macrophages or immature dendritic cells.

Primary human umbilical vein endothelial cells (HUVEC; BD Biosciences), maintained in Medium 200 (Cascade Biologics), are seeded in the upper chamber of a Transwell device (Corning) containing a microporous polycarbonate membrane (pore size 5 μm) pre-coated with fibronectin. The HUVEC endothelial cells on top of the porous membrane are grown to confluency (determined by phase-contrast light microscopy) and analyzed for the formation of tight-gap junctions and hence the formation of a physiological barrier (as determined by passive dye diffusion). Input cells of various sorts are added to the upper chamber. Input cells may be whole leukocytes (lymphocytes, monocytes, granulocytes, and neutrophils) isolated from normal peripheral blood by simple lysis of red blood cells; or peripheral blood mononuclear cells (PBMC; lymphocytes and monocytes) isolated by single-step density centrifugation using Histopaque-1077; or monocytes exclusively, isolated either by a second step of density centrifugation using 46% Percoll, or alternatively by immunomagnetic beads to deplete non-monocytic cells as per the art (MiltenyiBiotec). Briefly, in the case of mononuclear cells, PBMC are seeded at $1.0 \times 10^6$ cells onto the HUVEC monolayer in the upper chamber of the transwell device and allowed to bind for 1-2 hours at 37° C. in a standard $CO_2$ incubator. Unbound PBMC are removed by gentle washing with PBS. Remaining cells are allowed to transmigrate for 2-3 days, after which the upper chamber of the transwell (containing the HUVEC monolayer plus unmigrated cells) is removed, and transmigrated cells in the lower chamber are collected for analysis. Cells are pelleted by centrifugation and at this point can be stained with monoclonal antibodies to determine cell phenotype and subtype (e.g., CD14+CD16+ monocyte/macrophage versus CD19+ B lymphocyte). Cells are resuspended in 500 μl of PBS supplemented with 2% heat-inactivated fetal bovine serum and are analyzed using a FACSCalibur flow cytometer. In addition to phenotypic analysis, flow cytometry can determine the number of migrating cells expressed as a percentage of the number of input PBMC seeded onto the HUVEC monolayer by collecting data from each sample for one minute on a high flow rate. Alterations to this protocol include the pre-incubation of input cells with the X92 anti-IL-1alpha Ab to determine its potential neutralizing affect on the transmigration of membrane-bearing IL-1alpha leukocytes. Leukocytes positive for membrane-associated IL-1alpha would be predicted to ligate the IL-1R1 receptor expressed on resting HUVEC cells. Experimentally, after stimulation with IL-1alpha alone or with IL-1alpha preincubated with X92 Ab, adherent HUVECs would be removed from culture wells using a non-enzymatic reagent (e.g., EDTA or Cellstripper [Cellgro]), washed with PBS, and then analyzed by flow cytometry for the expression of CD54, CD62E, and CD106 adhesion molecules.

The addition of chemokines such as monocyte chemoattractant protein-1 (MCP-1) to the lower chamber of the transwell device can also be employed to study differences between spontaneous and chemotactic transmigration of leukocytes in the presence or absence of X92 Ab.

Human Subjects

The methods of the invention can be performed on any suitable human subject. Preferably, however, the subject will be one suffering from a condition associated with aberrant levels or function of CD14+CD16+ monocytes. Examples of such subjects include those with a pathology associated with aberrant function or levels of CD14+CD16+ monocytes such as an inflammatory condition, an autoimmune condition, cancer (e.g., breast, colorectal, prostate, ovarian, leukemia, lung, endometrial, or liver cancer), atherosclerosis, arthritis (e.g., osteoarthritis or rheumatoid arthritis), an inflammatory bowel disease (e.g., ulcerative colitis or Crohn's disease), a peripheral vascular disease, a cerebral vascular accident (stroke), one where chronic inflammation is present, one characterized by lesions having monocyte/macrophage infiltration, one where amyloid plaques are present in the brain (e.g., Alzheimer's disease), osteoporosis, amyotrophic lateral sclerosis, or multiple sclerosis.

EXAMPLES

Example 1

Flow Cytometry Experiments

Methods: Whole blood from a healthy donor was collected under aseptic conditions. 2.5 ml of whole blood was diluted 10 fold in lysis buffer (150 mM ammonium acetate 0.1 mM EDTA). The cells were kept in buffer on ice for 10 minutes and were then spun down at 1000 G for 5 min. Cells were resuspended in ice cold FACS buffer (PBS supplemented with 1% dry milk filtered through a 0.2 um filter). The cells were washed two times in FACS buffer. Pelleted cells were resuspended in 2.8 ml FACS buffer, counted using a hemocytometer, and under dim light fluorescently labeled antibodies added, according to the following scheme:

1) PerCP-Cy5.5 conjugated anti-CD14 (eBioscience™ affinity purified, mouse anti-human IgG, kappa, no. 45-109)
2) PE conjugated anti-CD16 (eBioscience™ affinity purified, mouse anti-human IgG1, no. 12-0168)
3) FITC conjugated anti-IL-1a (eBioscience™ affinity purified, mouse IgG1, anti-human IL-1a No. 11-718)
4) FITC conjugate anti-KLH (eBioscience™ affinity purified, mouse IgG1, kappa, no. 11-4714)
5) anti-CD14, anti-CD16
6) anti-CD14, anti-CD16, anti-IL-1a
7) anti-CD14, anti-CD16, anti-IL-1a, anti-KLH Suspended cells in 400 μl FACS buffer (approx. $1.5 \times 10^6$) were transferred to 1.5 ml eppendorf tubes and kept on ice shielded from light. Antibody was added (50 μl) and reacted with cells for 45 minutes. Cells were then washed by 3 rounds of centrifugation at 1000 G for 5 minutes and resuspended in 1.5 mL of FACS buffer and kept on ice until analyzed using a BD FACS analyzer.

Results: Whole peripheral blood cells (WPBC) were stained with anti-CD14 and anti-CD16 to identify a small subset of mononuclear cells. Using flow cytometry (FACS), CD14+CD16+ WPBC were further analyzed for the expression of interleukin-1alpha using a FITC-labeled anti-IL-1alpha specific monoclonal antibody. Remarkably, three-color FACS analysis revealed that virtually all of the IL-1alpha+ staining was in fact associated with the CD14+CD16+ population. Consequently, it was determined that the CD14+CD16+ cells and the IL-1alpha+ population of cells in the blood were largely the same population.

Example 2

Neutralization of Cell-Associated IL1A: MABP1 Blocks E-Selectin Expression on IL1-Stimulated HUVEC Cells MABp1 can inhibit the induced expression of cellular adhesion molecules on the surface of endothelial cells. MABP1-mediated inhibition of two key adhesion molecules, CD54 (ICAM-1) and CD62E (E-selectin), has been observed using human umbilical vein endothelial cells (HUVECs) as a model system. The MABp1 effect is most pronounced when HUVECs are stimulated not by soluble recombinant human IL1alpha but by membranous IL1alpha anchored by glycosyl-phosphatidylinositol (GPI) to the surface of engineered DG44 CHO cells (GPI-IL1A cells). In a representative experiment, confluent cultures of HUVEC cells in 6-well plates were co-cultured overnight with $5 \times 10^6$ GPI-IL1A DG44 cells in M-200 medium, either alone, in the presence of 10 µg/mL MABP1, or in the presence of 10 µg/mL D5 human IgG1 isotype control antibody. After 17-20 hours, HUVEC monolayers were washed extensively with Dulbecco's PBS and then lifted by non-enzymatic treatment for 20 minutes with CellStripper reagent (Cellgro Mediatech). Cells were immediately assayed for CD62E (E-selectin) expression using standard flow-cytometry protocols. Staining buffer comprised Dulbecco's PBS supplemented with 2% heat-inactivated fetal bovine serum. PE-conjugated mouse anti-human CD62E monoclonal antibody (eBioscience, clone P2H3) or a PE-conjugated mouse IgG1k isotype control (eBioscience, clone P3) were used per manufacturer's instructions to stain HUVEC cells in a 100 microliter staining volume for 20 minutes in the dark at room temperature. Two washes in staining buffer were subsequently performed and then samples were acquired on a FACSCalibur flow cytometer (BD Biosciences). Among n=3 experiments the upregulation of E-selectin on the surface of HUVEC cells induced by membranous GPI-IL1A was neutralized by MABP1 to baseline levels as exhibited by unstimulated HUVEC cells.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method comprising the steps of:
   (a) determining that a human subject with a disease or pathologic disorder has high levels of CD14+/CD16+ monocytes that contribute to the disease or pathologic disorder by removing a first sample of peripheral blood from the subject and performing flow cytometry on cells comprised within the first sample to assess the number or percent of CD14+/CD16+ monocytes in the first sample;
   (b) administering an agent that modulates the function or expression of interleukin-1alpha to the human subject; and
   (c) determining whether such administration modulates the amount of CD14+CD16+ monocytes in the subject by removing a second sample of peripheral blood mononuclear cells from the subject and performing flow cytometry on cells comprised within the second sample to assess the number or percent of CD14+/CD16+ monocytes in the second sample.

2. The method of claim 1, wherein the agent that modulates the function or expression of interleukin-1 alpha is one that interferes with interleukin-1 alpha binding to an interleukin-1 alpha receptor.

3. The method of claim 1, wherein the agent is an antibody that specifically binds interleukin-1 alpha.

4. The method of claim 3, wherein the antibody is a monoclonal antibody that specifically binds interleukin-1 alpha.

5. The method of claim 4, wherein the monoclonal antibody is a human antibody.

6. The method of claim 5, wherein the human antibody is an IgG1.

7. The method of claim 6, wherein the human antibody has a heavy chain comprising the amino acid sequence of SEQ ID NO:3 and a light chain comprising the amino acid sequence of SEQ ID NO:4.

8. The method of claim 1, wherein the human subject has a pathology associated with aberrant function or levels of CD14+CD16+ monocytes.

9. The method of claim 8, wherein the disease or pathologic disorder is an inflammatory condition.

10. The method of claim 8, wherein the disease or pathologic disorder is an autoimmune condition.

11. The method of claim 1, wherein at least 1.5% of the human subject's peripheral blood leukocytes are CD14+ CD16+ monocytes before administration of the agent and less than 1.5% of the human subject's peripheral blood leukocytes cells are CD14+CD16+ monocytes after administration of the agent.

12. The method of claim 1, wherein administration of the agent results in at least a 10% reduction in the percent of CD14+CD16+ monocytes in a complete blood count with differential.

13. The method of claim 1, wherein the step of determining whether such administration modulates the amount or function of CD14+CD16+ monocytes in the subject comprises assessing the function of the subject's CD14+CD16+ monocytes before and after administration of the agent.

14. The method of claim 13, wherein administration of the agent results in at least a 10% reduction in the function of CD14+CD16+ monocytes.

* * * * *